United States Patent [19]

Gerberich, Jr. et al.

[11] 4,011,252

[45] Mar. 8, 1977

[54] PRODUCTION OF FATTY ACIDS FROM ALKANES BY OXIDATION

[75] Inventors: Harold Robert Gerberich, Jr.; Edward F. Dougherty, both of Corpus Christi, Tex.

[73] Assignee: Celanese Corporation, New York, N.Y.

[22] Filed: Aug. 20, 1975

[21] Appl. No.: 606,280

[52] U.S. Cl. .................... 260/413; 260/530 R; 260/531 R

[51] Int. Cl.² ............... C07C 51/20; C07C 51/24; C07C 51/26; C07C 51/28

[58] Field of Search .......... 260/413, 409, 406, 423, 260/533 R, 452, 530 R, 531 R

[56] References Cited

UNITED STATES PATENTS

| | | | |
|---|---|---|---|
| 1,681,238 | 8/1928 | James | 260/413 |
| 1,721,959 | 7/1929 | James | 260/413 |
| 2,048,662 | 7/1936 | Luther et al. | 260/452 |
| 2,726,255 | 12/1955 | Walker et al. | 260/533 |
| 2,945,050 | 7/1960 | Franke et al. | 260/413 |
| 3,775,450 | 11/1973 | Washecheck et al. | 260/413 |

*Primary Examiner*—Patrick P. Garvin
*Assistant Examiner*—P. E. Konopka
*Attorney, Agent, or Firm*—Stewart N. Rice; Ralph M. Pritchett

[57] ABSTRACT

A process for producing fatty acids from $C_{20}$ to $C_{30}$ normal alkanes by air oxidizing the alkanes, followed by hydrogenating the product of the air oxidation and then oxidizing the hydrogenated product by nitric acid oxidation. The crude fatty acid product may be purified by a second hydrogenation to convert nitrogen impurities to amines and removal of the amines.

9 Claims, No Drawings

PRODUCTION OF FATTY ACIDS FROM ALKANES BY OXIDATION

BACKGROUND OF THE INVENTION

It is known, as described in co-pending U.S. patent application Ser. No. 586,761 filed by H. R. Gerberich, Jr., on June 13, 1975, to oxidize $C_{20}$ to $C_{30}$ normal alkanes with air and then to oxidize the air oxidation product further with nitric acid to form fatty acids. The fatty acid product recovered from such a process, however, contains nitrogenous impurities arising during the nitric acid oxidation which are desirably removed for most end uses of the fatty acids. At present, there is no simple and economical way known to remove substantially all of such nitrogen-containing impurities. It is known that some of these nitrogen-containing impurities may be converted to easily removable amine compounds by hydrogenating the crude fatty acid product; however many of the nitrogen-containing impurities are not converted to amines by hydrogenation, but remain in a difficulty-removable form.

It is thus an object of the present invention to produce an improved method of producing a fatty acid product from $C_{20}$ to $C_{30}$ normal alkanes involving a nitric acid oxidation, which fatty acid product may be purified relatively easily in order to remove nitrogen-containing impurities therefrom. It is an additional object of the present invention to provide a new and improved method for producing a fatty acid product from $C_{20}$ to $C_{30}$ normal alkanes involving a nitric acid oxidation, which fatty acid product is relatively free of nitrogen-containing impurities. Additional objects will become apparent from the following description of the present invention.

SUMMARY

The foregoing and additional objects are accomplished by the present invention which in one of its aspects is a process for the production of fatty acids which comprises: (a) oxidation of $C_{20}$ to $C_{30}$ normal alkanes with molecular oxygen at elevated temperatures and at pressures sufficient to maintain a liquid phase of said alkanes so as to produce an alkane oxidation product containing fatty acids, unreacted alkanes, and oxygenated hydrocarbon intermediates, said alkane oxidation product being comprised of an aqueous phase containing most of the $C_1$ to $C_6$ fatty acids and a hydrocarbon phase containing most of the $C_7$ and higher fatty acids; (b) hydrogenation of at least the said hydrocarbon phase of said alkane oxidation product by reacting same with molecular hydrogen under hydrogenation conditions utilizing a catalytic amount of a hydrogenation catalyst, the hydrogenation being carried to an extent sufficient to reduce the degree of unsaturation in the material being hydrogenated but insufficient to substantially affect the fatty acids contained therein; (c) oxidation by nitric acid oxidation of the product obtained in such hydrogenation so as to oxidize oxygenated hydrocarbon intermediates therein to fatty acids and produce a nitric acid oxidation product comprised of an aqueous phase containing most of the $C_1$ to $C_6$ fatty acids and a hydrocarbon phase containing most of the $C_7$ and higher fatty acids, said nitric acid oxidation being conducted at elevated temperatures and pressures sufficient to maintain a liquid phase and in the presence of a catalytic amount of a nitric acid oxidation catalyst; and (d) recovery of a fatty acid product from said nitric acid oxidation product. In another aspect the present invention involves a second hydrogenation of a crude fatty acid product so obtained to convert any nitrogen-containing impurities to amines, followed by removal of such amines.

DETAILED DESCRIPTION OF THE INVENTION

The present invention is applicable to the production of fatty acids from a $C_{20}$ to $C_{30}$ normal alkane, that is a straight-chain alkane containing from 20 to 30 carbon atoms. Usually a mixture of alkanes will be utilized, however, a single alkane may be utilized as feed if desired. By the term "fatty acids" is meant those straight-chain monocarboxylic acids free of unsaturation, that is straight-chain monocarboxylic alkanoic acids. The fatty acids produced according to the present invention may contain from 1 to 30 carbon atoms although most will be within the range of 2 to 25 carbon atoms.

The first step in the process for the production of a fatty acid includes the liquid phase oxidation of the alkane in the presence of molecular oxygen. This oxidation will sometimes hereinafter be referred to as the "air oxidation" since air is generally utilized as the source of molecular oxygen for economic reasons, although other sources of molecular oxygen may be used such as oxygen-enriched air or technically pure oxygen itself. The temperatures involved in the air oxidation may vary widely, for example, within the range of about 100° to 300° C but are preferably within the range of about 110° to 140° C. The pressure needs to be only sufficient to maintain a liquid phase of the alkanes which, of course, will vary according to the temperature utilized. Generally, pressures within the range of about 1 to 200 atmospheres absolute may be utilized although pressures within the range of about 1 to 20 atmospheres absolute are preferred and are more economical. Atmospheric pressure is especially preferred.

The air oxidation may be accomplished either with or without a catalyst, although it is preferable to use an oxidation catalyst of any of the well known types generally employed in an oxidation utilizing molecular oxygen. Catalyst systems include those containing cobalt, manganese, potassium, chromium, nickel, copper or mixtures thereof. A catalyst containing both potassium and manganese is preferred, potassium permanganate being a suitable source of such a catalyst. These catalysts are generally utilized such that the catalyst metals are present in amount of from about 10 to 10,000 parts per million, preferably about 100 to 1,500 parts per million, by weight of the weight of the reaction mixture. Residence or reaction times vary according to temperature, pressure, feed composition and the like, but are generally on the order from 0.5 to 20 hours, more usually from about 2 to 10 hours.

The alkane oxidation product, that is the product produced by the air oxidation, is a two phase liquid which contains a wide mixture of compounds including fatty acids ranging from $C_1$ to $C_{30}$ acids and also includes oxygenated hydrocarbon intermediates and some unreacted alkanes. One phase is an aqueous phase containing most of the $C_1$ to $C_6$ fatty acids and the other phase is a non-aqueous or hydrocarbon phase containing unoxidized alkane hydrocarbons and the higher fatty acids (for example, $C_7$ and above). Both phases also contain oxygenated hydrocarbon intermediates. It has been discovered by the inventors herein, and such forms a basis of the present invention, that there is also in the air oxidation product a significant amount of unsaturation present, it having also been discovered by the inventors herein that the amount of such unsaturation corresponds roughly to the amount of nitrogen-containing compounds in the final fatty acid product (following nitric acid oxidation) which cannot be converted to amines for easy removal as discussed above. It is theorized that unsaturated linkages react during the nitric acid oxidation to form a type of nitrogen-containing compound which is not convertible to an amine by hydrogenation. The present invention lies in the step of mildly hydrogenating the product of the air oxidation to reduce, and preferably eliminate, any unsaturation present, the hydrogenation being prior to the nitric acid oxidation step. By doing so, a greater amount of the nitrogen containing impurities in the fatty acid product separated from the nitric acid oxidation product can be removed via a hydrogenation.

The hydrogenation of the air oxidation product is conducted according to known hydrogenation procedure. It can advantageously be carried out by feeding the product of the air oxidation, including both phases and without the necessity of any separation steps, together with hydrogen to a reaction zone maintained at a temperature within the range of about 100° to 325° C, preferably about 200° to 300° C, and a pressure within the range of about 1 to 200 atmospheres absolute, preferably 75 to 175 atmospheres absolute. The entire air oxidation product is preferably hydrogenated, although if desired, the aqueous phase may be separated from the non-aqueous phase and only one of such phases hydrogenated. Since most of the unsaturation is present in the non-aqueous phase, at least this phase, if none other, should be hydrogenated.

The hydrogenation should be conducted in the presence of a hydrogenation catalyst, substantially any of the known hydrogenation catalysts being operable. Suitable hydrogenation catalysts include those of copper, copper chromite, nickel, cobalt, platinum, or palladium or mixtures thereof. Preferred catalysts are those of platinum or palladium or mixtures thereof. The catalyst may be unsupported or supported on a known support such as carbon, and the like.

The hydrogenation may be carried out in conventional fashion as in a fixed, flooded catalyst bed, a slurry catalyst bed, or a trickle catalyst bed. The hydrogenation is carried out such that it causes a reduction in the degree of unsaturation in the alkane oxidation product (or portion thereof being hydrogenated), preferably reducing the amount of unsaturation by at least 85% although any reduction, e.g. only at least 50%, will be helpful. The hydrogenation should not be so harsh as to adversely affect the fatty acids present. Generally the residence or reaction time for the hydrogenation of the alkane oxidation product should be within the range of about 1 to 20 hours.

The product obtained in the hydrogenation is then subjected to a nitric acid oxidation. Conventional nitric acid oxidation techniques may be utilized and this will generally involve mixing the product of the hydrogenation with from about 0.1 to 10 times, preferably about 0.5 to 3.0 times, its weight of an aqueous nitric acid solution. The aqueous nitric acid solution will generally be of a concentration of about 40 to 70 percent by weight nitric acid. There will also be added a nitric acid oxidation catalyst, practically any of the known oxidation catalysts such as those containing cobalt, nickel, iron, chromium, manganese, copper, vanadium or mixtures thereof. Preferred is a copper-vanadium catalyst, such usually being added as ammonium metavandate and copper turnings. The total amount of catalyst metals should generally be within the range of about 0.1 to 1.0 percent by weight of the reaction mixture.

Temperatures for the nitric acid oxidation should generally range from about 60° to 130° C and preferably within the range of about 75° to 95° C. The pressure needs to be only sufficient to maintain a liquid phase and generally would be within the range of about 1 to 20 atmospheres absolute, preferably about 1 to 5 atmospheres absolute.

The purpose of the nitric acid oxidation is to oxidize any partially oxidized alkanes, herein referred to as oxygenated hydrocarbon intermediates, to fatty acids which were not so oxidized in the air oxidation step. The effluent or product of the nitric acid oxidation will be a two phase system containing fatty acids, water, unreacted alkanes, nitrogen-containing impurities, various oxygenated compounds other than fatty acids, and the like. A fatty acid product may be recovered from this reaction mixture by known methods which may include subsequent purification steps. One phase of the nitric acid oxidation will consist of an aqueous nitric acid phase containing most of the $C_1$ to $C_6$ fatty acids and a non-aqueous or hydrocarbon phase containing most of the higher fatty acids (i.e. $C_7$ and above). If only the hydrocarbon phase of the air oxidation, that is the phase containing the higher fatty acids, has been passed to the nitric acid oxidation via the prehydrogenation zone, then the amount of lower fatty acids in the aqueous phase of the nitric acid oxidation effluent will be lower than if both the aqueous and hydrocarbon phases of the air oxidation had been further processed. Fatty acids may be recovered from the aqueous nitric acid phase by solvent extraction, such as with benzene, cyclohexane or the like followed by evaporation of the solvent.

The traditional method of recovering the higher fatty acids from the hydrocarbon phase is by addition of an excess of an aqueous caustic solution to convert the acids to sodium salts followed by separation of the aqueous solution of the sodium salts and then "springing" the fatty acids by addition of sulfuric acid. The fatty acids are then further purified by vacuum distillation. The traditional method in many instances is not the most economical due to the high cost of caustic and sulfuric acid. Also disposal of sodium sulfate is a problem. Solvent extraction may be used in lieu of the traditional method of recovering the higher fatty acids from the hydrocarbon phase. A wide variety of solvents will accomplish the extraction such as the lower alkanols, lower dialkyl ethers and lower dialkyl ketones and aqueous solutions thereof. Alcohols, however, have the disadvantage of forming esters with fatty acids due to trace amounts of nitric acid usually present which serves as a catalyst for the esterification. The preferred solvent is a mixture of a lower dialkyl ketone and water, especially acetone and water. The volume ratio of acetone to water may vary widely, for example, from about 1:1 to 7:1, although preferably from about 1.5:1 to 6:1. Sufficient water must be present to effect separation of the hydrocarbon-rich and acetone-rich phases, although too much water will cause an unfavorable distribution coefficient. To minimize the extraction of hydrocarbons in a continuous extraction process, a short chain hydrocarbon ($C_7$–$C_{11}$ alkanes) may be fed countercurrent to the acetone-rich phase to displace the higher molecular weight hydrocarbon. The acetone, water and short chain hydrocarbon may then be distilled away from the fatty acids and the latter further purified by vacuum distillation.

The fatty acid product recovered from the nitric acid oxidation, unless subsequent purification techniques are utilized, will contain amounts of nitrogen-containing compounds as impurities. Frequently, these nitrogen-containing compound impurities will be present in such amounts as to provide 3% by weight or more of nitrogen. For many uses of the fatty acids, these nitrogeneous impurities must be substantially eliminated and it is known to accomplish such by hydrogenating the nitrogen compounds to amines which are relatively easily removable. When operating according to prior art and without the prehydrogenation of the air oxidation product according to the present invention, a substantial part of the nitrogen-containing impurities cannot be readily converted to amines by hydrogenation and thus are extremely difficult of removal. Most of such nitrogen-containing impurities which are not readily converted to amines will be in the higher fatty acids ($C_7$ and above) recovered from the hydrocarbon phase of the nitric acid oxidation. According to the present invention, practically all of the nitrogen-containing compound impurities may be converted to amines by hydrogenation.

The second hydrogenation, that is the hydrogenation of the fatty acid product separated from the nitric acid oxidation effluent, or at least the fatty acids from the hydrocarbon phase of the nitric acid oxidation, may be accomplished in the same manner and utilizing the generally same conditions, catalysts and the like as the hydrogenation discussed above wherein the air oxidation product is hydrogenated. Conditions in the second hydrogenation are, however, preferably slightly milder than the hydrogenation of the air oxidation product. Thus, suitable temperature range from 50° to 300° C, preferably about 100° to 250° C, and suitable pressures range from about 1 to 200, preferably 50 to 150, atmospheres absolute.

Following the hydrogenation of the fatty acid product, the amines formed in the hydrogenation may be removed by conventional and known techniques to result in a fatty acid product of improved purity. For example, the amines may be removed by reaction with an aqueous solution of a strong acid to form an amine salt which will concentrate in the resulting aqueous phase. Suitable acids for such purpose include phosphoric, sulfuric and hydrochloric. An alternative method of amine removal is by ion exchange means wherein the amine-containing fatty acids are passed through a bed of a strong acid ion exchange resin. Use of an ion exchange resin avoids the possibility of emulsion formation which can occur when an aqueous solution of a strong acid is used.

EXAMPLE

To a continuous reactor were fed 368 liters (measured at STP) per hour of air, 1.0 liter (liquid) per hour of a mixture of $C_{20}$–$C_{22}$ normal alkanes and 0.39 grams per hour of potassium permanganate catalyst. The average residence time was 8 hours and the reaction temperature and pressure were 122° C and 2.36 atmospheres absolute, respectively. Upon analysis of the recovered product, it was found that 23 mole percent of the hydrocarbon had been oxidized of which 39 mole percent had been converted to monocarboxylic acids. The remaining product was aldehydes, ketones, alcohols, esters, carbon oxides, and multifunctional compounds. Then, 500cc. of reactor effluent (both phases) was reduced with hydrogen for 15 hours at 216° C and 89 atmospheres absolute over 5.0 grams of 5 weight percent palladium on carbon catalyst. This decreased the unsaturation as determined by the iodine number from 48.2 mg.$I_2$/g. to 2.8 mg.$I_2$/g.

The hydrogenated product (500cc.) was added over a 20 minute period to 1,000cc. of 70 weight percent nitric acid containing 2.0 grams of ammonium metavanadate ($NH_4VO_3$) and 1.0 gram of copper (II). The temperature was maintained at 80°-85° C during the period of addition and for one hour afterwards. The product phases were separated and the hydrocarbon phase washed with water to remove nitric acid and soluble nitrogen oxides. Analysis of both product phases of the nitric acid oxidation product showed that as a result of the nitric acid oxidation the effective molar efficiency of monocarboxylic acids was increased to 75% based on the fraction of hydrocarbon oxidized in the air oxidation step.

The hydrocarbon phase (500cc.) containing the $C_7$ and above monocarboxylic acids was then extracted five times at 25° C with 310cc. portions of a solution of 70 parts acetone and 30 parts water by volume. After removal of the acetone and water by distillation, the recovered fatty acids were found to contain 0.69 weight percent nitrogen by Kjeldahl analysis.

The recovered fatty acids were hydrogenated to convert the nitrogen functionalities to amines. The fatty acids (50 grams) were treated with hydrogen (135 atmospheres absolute) for 18 hours at 250° C over a 5 weight percent palladium on carbon catalyst (0.5 gram). Upon washing the reduced product with dilute aqueous sulfuric acid the nitrogen content was found to be less than 0.05 weight percent by Kjeldahl analysis.

When the hydrogenation of the air oxidized product was omitted, the fatty acids recovered from the nitric acid oxidation step contained 0.6 to 1.0 weight percent nitrogen. Subsequent reduction with hydrogen and washing with dilute mineral acid gives a fatty acid product containing 0.3 to 0.6 weight percent nitrogen.

The embodiments of the invention in which an exclusive property or privilege is claimed are defined as follows:

1. A process for the production of fatty acids which comprises:
   a. oxidation of $C_{20}$ to $C_{30}$ normal alkanes with molecular oxygen at elevated temperatures and at pressures sufficient to maintain a liquid phase of said alkanes so as to produce an alkane oxidation product containing fatty acids, unreacted alkanes, and oxygenated hydrocarbon intermediates, said alkane oxidation product being comprised of an aqueous phase containing most of the $C_1$ to $C_6$ fatty acids and a hydrocarbon phase containing most of the $C_7$ and higher fatty acids;
   b. hydrogenation of at least the said hydrocarbon phase of said alkane oxidation product by reacting same with molecular hydrogen under hydrogenation conditions utilizing a catalytic amount of a hydrogenation catalyst, the hydrogenation being carried to an extent sufficient to reduce the degree of unsaturation by at least 50% as measured by the iodine number in the material being hydrogenated but insufficient to substantially affect the fatty acids contained therein;

c. oxidation by nitric acid oxidation of the product obtained in such hydrogenation so as to oxidize oxygenated hydrocarbon intermediates therein to fatty acids and produce a nitric acid oxidation product comprised of an aqueous phase containing most of the $C_1$ to $C_6$ fatty acids and a hydrocarbon phase containing most of the $C_7$ and higher fatty acids, said nitric acid oxidation being conducted at elevated temperatures and pressures sufficient to maintain a liquid phase and in the presence of a catalytic amount of a nitric acid oxidation catalyst; and d. recovery of a fatty acid product from said nitric acid oxidation product.

2. The process of claim 1 wherein said hydrogenation is accomplished using a hydrogenation catalyst of palladium or platinum, is conducted at temperatures within the range of about 200° to 300° C and at pressures within the range of about 75 to 175 atmospheres absolute, and is sufficient to reduce the said degree of unsaturation by at least about 85%.

3. The process of claim 1 wherein said oxidation of said alkanes with molecular oxygen is accomplished at temperatures within the range of about 110° to 140° C and at pressures within the range of about 1 to 20 atmospheres absolute, utilizing an oxidation catalyst containing potassium or manganese or mixtures thereof, and utilizing air or oxygen-enriched air as the source of molecular oxygen.

4. The process of claim 1 wherein said nitric acid oxidation is conducted at temperatures within the range of about 75° to 95° C and pressures of about 1 to 20 atmospheres absolute, and utilizing a nitric acid oxidation catalyst containing copper or vanadium or mixtures thereof.

5. The process of claim 2 wherein said oxidation of said alkanes with molecular oxygen is accomplished at temperatures within the range of about 110° to 140° C and at pressures within the range of about 1 to 20 atmospheres absolute, utilizing an oxidation catalyst containing potassium or manganese or mixtures thereof, and utilizing air or oxygen-enriched air as the source of molecular oxygen, and, wherein said nitric acid oxidation is conducted at temperatures within the range of about 75° to 95° C and pressures within the range of about 1 to 20 atmospheres absolute utilizing a nitric acid oxidation catalyst containing copper or vanadium or mixtures thereof.

6. The process of claim 5 wherein both phases of said alkane oxidation product are subjected to said hydrogenation.

7. A process for the production of fatty acids which comprises: (a) oxidation of $C_{20}$ to $C_{30}$ normal alkanes with molecular oxygen at elevated temperatures and at pressures sufficient to maintain a liquid phase of said alkanes so as to produce an alkane oxidation product containing fatty acids, unreacted alkanes, and oxygenated hydrocarbon intermediates, said alkane oxidation product being comprised of an aqueous phase containing most of the $C_1$ to $C_6$ fatty acids and a hydrocarbon phase containing most of the $C_7$ and higher fatty acids; (b) hydrogenation of at least the said hydrocarbon phase of said alkane oxidation product by reacting same with molecular hydrogen under hydrogenation conditions utilizing a catalytic amount of a hydrogenation catalyst, the hydrogenation being carried to an extent sufficient to reduce the degree of unsaturation by at least 50% as measured by the iodine number in the material being hydrogenated but insufficient to substantially affect the fatty acids contained therein; (c) oxidation by nitric acid oxidation of the product obtained in such hydrogenation so as to oxidize oxygenated hydrocarbon intermediates therein to fatty acids and produce a nitric acid oxidation product comprised of an aqueous phase containing most of the $C_1$ to $C_6$ fatty acids and a hydrocarbon phase containing most of the $C_7$ and higher fatty acids, said nitric acid oxidation being conducted at elevated temperatures and pressures sufficient to maintain a liquid phase and in the presence of a catalytic amount of a nitric acid oxidation catalyst; (d) separation of a crude fatty acid product comprised at least of the fatty acids contained in said hydrocarbon phase of said nitric acid oxidation product; (e) hydrogenation of said crude fatty acid product to convert at least a portion of nitrogen-containing compound impurities therein to amines; and (f) removal of said amines from said crude fatty acid product to obtain a fatty acid product of improved impurity.

8. The process of claim 7 wherein said hydrogenation of at least the said hydrocarbon phase of said alkane oxidation product is accomplished using a hydrogenation catalyst of palladium or platinum, is conducted at temperatures within the range of about 200° to 300° C and at pressures within the range of about 75 to 175 atmospheres absolute, and is sufficient to reduce the said degree of unsaturation by at least about 85%.

9. The process of claim 8 wherein said oxidation of said alkanes with molecular oxygen is accomplished at temperatures within the range of about 110° to 140° C and at pressures within the range of about 1 to 20 atmospheres absolute, utilizing an oxidation catalyst containing potassium or manganese or mixtures thereof, and utilizing air or oxygen-enriched air as the source of molecular oxygen; and, wherein said nitric acid oxidation is conducted at temperatures within the range of about 75° to 95° C and pressures within the range of about 1 to 20 atmospheres absolute utilizing a nitric acid oxidation catalyst containing copper or vanadium or mixtures thereof; and wherein said hydrogenation of said crude fatty acid product is accomplished using a hydrogenation catalyst of palladium or platinum, and is conducted at temperatures within the range of about 100° to 250° C and at pressures within the range of about 50 to 150 atmospheres absolute.

* * * * *